United States Patent [19]
Narayanan et al.

[11] B 3,983,130
[45] Sept. 28, 1976

[54] ANTHELMINTIC ISOTHIOCYANOBENZOXAZOLES

[75] Inventors: Venkatachala Lakshmi Narayanan, Hightstown; Rudiger D. Haugwitz, Titusville, both of N.J.

[73] Assignee: E. R. Squibb & Sons, Inc., Princeton, N.J.

[22] Filed: July 8, 1974

[21] Appl. No.: 486,280

[44] Published under the second Trial Voluntary Protest Program on February 3, 1976 as document No. B 486,280.

Related U.S. Application Data

[63] Continuation of Ser. No. 259,057, June 2, 1972, abandoned.

[52] U.S. Cl. ......................... 260/307 D; 260/250 R; 260/256.5 R; 260/294.8 C; 260/302 H; 424/250; 424/251; 424/263; 424/270; 424/272
[51] Int. Cl.² ......................................... C07D 263/56
[58] Field of Search ............................. 260/307 D

[56] References Cited
UNITED STATES PATENTS

| | | | |
|---|---|---|---|
| 2,075,359 | 3/1937 | Saltzberg et al. | 424/250 |
| 3,231,596 | 1/1966 | Knusli | 260/454 |
| 3,341,564 | 9/1967 | Potts et al. | 260/454 |
| 3,342,846 | 9/1967 | Cometti | 424/302 |
| 3,558,784 | 1/1971 | Paltauf et al. | 424/302 |
| 3,586,670 | 6/1971 | Brenneisen et al. | 260/340 |
| 3,637,734 | 1/1972 | Harnisch | 260/307 |

FOREIGN PATENTS OR APPLICATIONS

| | | |
|---|---|---|
| 515,789 | 12/1952 | Belgium |
| 1,453,247 | 8/1966 | France |
| 515,789 | 12/1952 | Belgium |
| 1,198,941 | 7/1970 | United Kingdom |

OTHER PUBLICATIONS

Brenneisen et al. —C. A. 78, 58423s, (1973).

*Primary Examiner*—Raymond V. Rush
*Attorney, Agent, or Firm*—Lawrence S. Levinson; Merle J. Smith; Donald J. Barrack

[57] ABSTRACT

Isothiocyanobenzoxazoles are provided having the structure

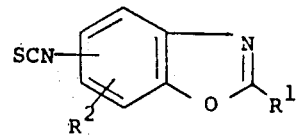

wherein $R^1$ and $R^2$ are as defined hereinafter and which are useful as anthelmintic agents and disinfectants.

10 Claims, No Drawings

ANTHELMINTIC ISOTHIOCYANOBENZOXAZOLES

This is a continuation of U.S. Pat. application Ser. No. 259,057, filed June 2, 1972, and now abandoned.

The present invention relates to isothiocyanobenzoxazoles having the structure

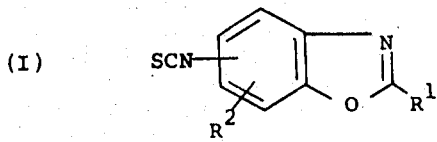

(I)

wherein $R^1$ is hydrogen, lower alkyl, cycloalkyl or a substituted or unsubstituted N-, S- or O-heterocyclic ring containing 5 or 6 members and 1 or 2 heteroatoms such as thiophene, furan, thiazole, pyridine, pyrazine, oxazole or pyrimidine and $R^2$ is hydrogen, lower alkyl, halogen or lower alkoxy.

The lower alkyl groups represented by the above groups include straight or branched chain aliphatic hydrocarbon radicals having up to and including seven carbon atoms, such as methyl, ethyl, propyl, isopropyl, butyl, isobutyl, t-butyl, amyl, hexyl, heptyl and the like. The lower alkyl groups can include as substituents any of the aryl groups mentioned below as well as halogen.

The alkoxy group includes straight and branched chain radicals of up to and including seven carbon atoms, corresponding to the above alkyl groups, e.g., methoxy ethoxy, propoxy, isopropoxy and the like.

The term "halogen" includes each of the four halogens but fluorine and chlorine are preferred.

The term cycloalkyl includes saturated carbocyclic ring systems containing 3 to 6 carbons such as cyclopropyl, cyclobutyl, cyclopentyl and cyclohexyl.

The heterocyclic ring may be substituted with lower alkyl, halogen, acetoxyalkyl or di-lower alkylaminoalkyl.

The di-lower alkylaminoalkyl groups include dimethylaminoethyl, diethylaminopropyl, ethylmethylaminopropyl, butylmethylaminoethyl and ethylpropylaminobutyl. However, it will be understood that the lower alkyl can be any other of the above alkyl groups.

Exemplary of compounds falling within the present invention include, but are not limited to, the following set out in Table A below:

TABLE A

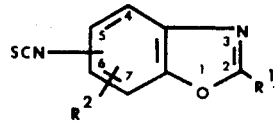

| | $R^1$ | $R^2$ (position) | SCN position |
|---|---|---|---|
| 1. | N-CH₃ (pyrrole) | H | 5 |
| 2. | furan | H | 5 |
| 3. | thiophene | H | 5 |
| 4. | 2-methylpyridine | H | 5 |
| 5. | thiazole | Cl (5) | 6 |
| 6. | 5-methylfuran | CH₃ (4) | 6 |
| 7. | cyclopropyl | H | 5 |
| 8. | cyclohexyl | H | 5 |
| 9. | pyridine | H | 6 |
| 10. | oxazole | H | 5 |

Preferred compounds are compounds 1. to 3. set out in Table A above.

The isothiocyanobenzoxazoles of the formula (I) are prepared by reacting a benzoxazole substituted by a primary amino group in the ring, that is

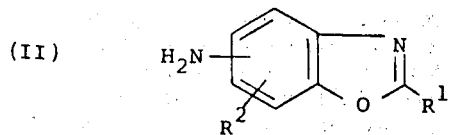

(II)

with a reagent capable of introducing a thiocarbonyl group into the amino group, in the presence of a solvent or diluent which is inert to the reactants.

Thus, for example, the aminobenzoxazole of formula (II) can be reacted with a thiocarbamic acid derivative of the structure (III)     Hal—CS—Y wherein Hal is Cl or Br and Y represents Cl, Br or a dialkylamino group. Examples of compounds of formula (III) include thiophosgene and N,N-diethylthiocarbamoyl chloride.

Where thiophogene is employed in the above reaction, the reaction is carried out at temperatures ranging from about 0° to about 60°C preferably in the presence of an acid binding agent such as calcium carbonates, triethylamine or sodium carbonate, according to the procedure described in Houben-Weyl's *Methoden Der Organischen Chemie*, 4th Edition, Vol. 9 pages 867 and ff (1955) and according to O. E. Schultz in Arch. Pharm. 295, 146–151 (1962).

Where N,N-diethylthiocarbamoyl chloride is employed to react with the aminobenzoxazole, the reaction is carried out at temperatures ranging from about 40° to about 200°C according to the procedure described in J. Org. Chem. 30, 2465 (1965).

Compounds of formula (I) may also be prepared by reacting an aminobenzoxazole (II) with a bis-thiocarbamoyl sulfide

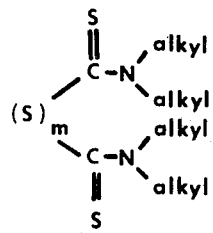

wherein m is 1 or 2 and alkyl is lower alkyl preferably ethyl, in the presence of a hydrogen halide according to F. H. Marquardt, Helv. Chim. Acta, 49, 1716.

In another method for preparing compounds of formula (I), the aminobenzoxazole (II) is reacted with bis-trichloromethyl pentathiodipercarbonate according to the procedure described by R. Gottfried, Angew. Chem. 78, 985 (1966).

In still another method for preparing compounds of formula (I), the aminobenzoxazole (II) is reacted with ammonium rhodanide in the presence of gaseous hydrogen chloride according to British Patent No. 1,099,768.

The compounds of formula (I) can also be formed by reacting the aminobenzoxazole (II) with phosgene and phosphorus pentasulfide according to Houben-Weyl, supra, Vol. 9, pages 867 and ff (1955).

Compounds of formula (I) can also be prepared by reacting the aminobenzoxazole (II) with carbon disulfide in the presence of an inorganic or organic base, whereby the amino group is first converted into the corresponding dithiocarbamic salt which is subsequently dehydrosulfurised to the isothiocyano group. The dehydrosulfurization following the reaction with carbon disulfide and base can be performed oxidatively with metal salts (British Patent No. 793,802, Dutch Pat. No. 81,326) e.g. with lead, copper, zinc or iron III-salts, iodine, alkali metal hypochlorites or chlorites, preferably with sodium and potassium salts (French Pat. No. 1,311,855), or with suitable acid halides such as phosgene and phosphorus oxychloride (D. Martin, et al., Chem. Ber. 98, 2425-2426 (1965)), or with $Cl_2$ and ammonium sulfide (DAS No. 1,192,189 or with chloramine T (British Patent No. 1,024,913).

In yet another method for preparing the compounds of formula (I), the aminobenzoxazole (II) can be reacted with ammonium rhodanide and benzoyl chloride leading first to the thiourea derivative which is then thermally decomposed, e.g., in boiling chlorobenzene, to the isothiocyano derivative. This reaction is performed, e.g., according to Houben-Weyl, supra, 4th Edition, Vol. 9, page 867 and ff (1955).

Compounds of formula (I) can also be prepared by reacting the aminobenzoxazole (II) with carbon disulfide and dicyclohexylcarbodiimide in the presence of a tertiary amine according to J. C. Jochims, Chem. Ber. 101, 1746 (1968).

The aminobenzoxazoles (II) are most conveniently prepared by reducing their corresponding nitro derivative (V)

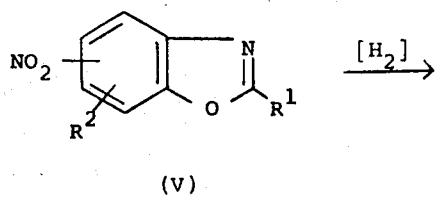

(V)

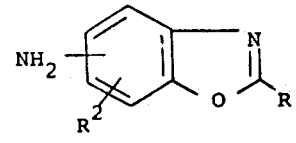

(II)

The nitrobenzoxazoles (V) serving as starting material for (II) can be prepared according to the following known processes:

1. The most general procedure (A. Ladenburg, Ber., 1876, 9, 1524: M. A. Phillips, J. Soc. Chem. Ind., 1937, 56, 474) comprises heating o-aminophenols with carboxylic acids, their chlorides, anhydrides or other derivatives including aldehydes, amides (St. von Niementowski, Ber. 1897, 30, 3064: S. Skraup, Ann., 1919, 419, 80; Ber., 1922, 55, 1097), nitriles (E. L. Holljes and E. C. Wagner, J. Org. Chem., 1944, 9, 31), amidines (E. C. Wagner, ibid., 1940, 5, 133) and iminoether hydrochlorides (F. E. King and R. M. Acheson, J. Chem. Soc., 1949, 1396).

2. The anti-oximes of o-hydroxyphenylketones yield benzoxazoles as products of Beckmann transformations (cf. J. Meisenheimer, et al., J. Pr. Chem., 1928, [ii], 119, 315).

3. 2-Arylbenzoxazoles are produced by lead tetraacetate oxidation of Schiff's bases derived from o-aminophenols and arylaldehydes (F. Stephens and J. D. Bower, J. Chem. Soc., 1949, 2917; 1950, 1722).

4. Interaction of p-nitrophenylazides with acetic and polyposphoric acids leads to 2-methyl-6-nitrobenzoxazoles. (R. Garner, et al., J. Chem. Soc., 1960, 1980).

Other applicable procedures are generally discussed in "Benzoxazoles and Related Systems," "Heterocyclic Compounds," ed. R. C. Elderfield, Vol. 5, p. 418 and "Benzoxazoles," "Chemistry of Carbon Compounds," ed. E. H. Rood, Vol. IV-A, p. 375.

The compounds of formula (I) form physiologically acceptable acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic acid. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate, and the like.

The benzoxazoles described herein have anthelmintic activity and are useful in the treatment and/or prevention of helminthiasis, a parasitic disease which causes widespread and often serious infection in domesticated animals such as swine, horses, cattle, sheep and goats. In treating domesticated animals, the compounds may be mixed with a nontoxic, edible carrier to form a feed supplement which is then incorporated in the animal feed in the desired concentration, or they may be administered in unit dosage forms which, in the case of large domesticated animals, take the form of boluses, or in the form of a liquid drench. Alternatively, water-soluble salts or a dispersable, wettable powder containing the anthelmintic agent may be added to the drinking water of the animals.

The preferred dosage level for treating a helminth infection will depend to a large extent on the particular benzoxazole compound being employed, on the severity of the infection and on the particular species of animal to be treated. In general, the benzoxazoles exhibit anthelmintic activity when administered to animals in a daily dose of about 50 to about 300 mg. per kilogram of animal body weight. It is preferred to employ in the range of 100-200 mg. per kilogram of body weight per day. The compounds may be given in a single dose or divided into a plurality of smaller doses. If desired, the course of treatment may be extended over a period of days in which case the optimum daily dose level may be lowered. When the compouds are to be employed primarily as prophylactic agents for the prevention of helminthic infections, the preferred daily dose level is, of course, lower than the therapeutic level is, preferably in the range of about 10-70 mg. per kilogram of body weight. The benzoxazoles may be incorporated in the animal feeds, and this method of administration is preferred when the compounds are to be used prophylactically, in which case they are incorporated in the feeds at concentrations such that the animal will consume daily from about 10 to about 70 mg. of benzoxazole per kilogram of body weight.

The means employed for administering these benzoxazoles to animals are not critical, and any of the methods now used or available for treating animals infected with or susceptible to parasitic infections are satisfactory. When these substances are employed therapeutically to treat an established infection, they are conveniently administered in a unit dosage form such as in a capsule, bolus, tablet, or as a liquid drench. It will be noted that all of these methods contemplate oral administration, since this is the most effective method of treating the worm-infected stomach or intestinal tract.

When the benzoxazoles are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like. These unit dosage formulations may be widely varied with respect to their total weight and content of anthelmintic agent, depending on factors such as the type of host animal to be treated, the dose level desired, and the severity and type of parasitic infestation. For large animals such as sheep, swine or cattle, boluses weighing up to 15 grams may be used, although it is preferred to employ boluses weighing from 2-10 grams and containing from 1-5 grams of the anthelmintic agent. These boluses, as well as smaller size tablets, contain binders and lubricants, and are compounded by techniques known in this art. Capsules are readily prepared by mixing the active ingredient with a diluent such as starch or lactose andn filling into the capsule.

In order to treat infected animals by means of a drench, the benzoxazoles are mixed with a suspending agent such as bentonite and the solid product added to water just prior to administration. The preferred drenches in accordance with this invention contain from about 5-50 percent by weight of benzoxazole compound.

The benzoxazoles described herein may also be administered as a component of the feed of the animals or dissolved or suspended in the drinking water. According to the invention, novel feed and feed supplement compositions are provided in which compounds of Formula (I) above are present as an active anthelmintic ingredient. Such compositions comprise the benzoxazoles intimately dispersed in or admixed with an inert carrier or diluent, i.e. one that is nonreactive with respect to the benzoxazole and that may be administered with safety to the animals. The carrier or diluent is preferably one that is or may be an ingredient of the animal ration.

In the feed supplement compositions the active ingredient is present in relatively large amounts. These supplements are suitable for addition to the feed either directly or after an intermediate dilution or blending step. Examples of carriers or diluents suitable for such compositions are solid orally ingestible carriers such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone and the like. The anthelmintic agents are intimately dispersed or admixed throughout the solid inert carrier by methods such as grinding, stirring, milling, or tumbling. By selecting proper diluents and by altering the ratio of carrier to active ingredient, compositions of any desired concentration may be prepared. Formulations containing from about 5% to about 50% by weight, and preferably from about 10-30% by weight, of active ingredient are particularly suitable for addition to feeds. The active compound is normally dispersed or mixed uniformly in the diluent but in some instances may be sorbed on the carrier.

Feed supplements are prepared by uniformly mixing the appropriate benzoxazoles with the carriers. Such supplements are added to the finished animal feed in an amount adequate to give the final concentration desired for controlling or treating helminthiasis by way of the animal ration. Although the preferred level in feeds will depend on the particular compound being employed, the anthelmintic compounds of this invention are normally fed at levels of 0.10–2.0 percent in the feed. One advantageous method of administering the compounds of this invention to animals whose feeds are conviently pelleted, such as sheep, is to incorporate them directly in the pellets. For instance, benzoxazoles are readily incorporated in nutritionally adequate alfalfa pellets (during the pelleting operation) at levels of 0.5 to 5 grams per pound of pellets for therapeutic use, and at lower levels for prophylactic use, and such pellets fed to the worm-infested animals. Alternatively, the benzoxazoles may be incorporated in salt licks or salt blocks at any desired concentration (concentrations of 5-25% by weight are conveniently employed). Large animals such as sheep, cattle and goats, then receive the anthelmintics with their salt.

The following examples further illustrate and represent preferred embodiments of the invention.

EXAMPLE 1

Isothiocyanic acid, 2-(2-furyl)-5-benzoxazolyl ester.

Step A 15.4 g of 4-nitro-2-aminophenol is dissolved in 250 ml of ethanol and to this solution 9.6 g of furaldehyde is added to room temperature. The reaction is allowed to stir at room temperature for 0.25 hr and the precipitated crystals are collected. The resulting Schiff Base is then dissolved in 250 ml of glacial acetic acid, treated with 44 g of lead tetraacetate and then refluxed for 2 hr. The mixture is then diluted with 250 ml of water and the precipitated product is collected and washed with water. Recrystallization from 150 ml of $CH_2Cl_2$ yields 10.1 g of 5-nitro-2-(2-furyl)benzoxazole, mp 175°–177°.

Anal. Calc'd for $C_{11}H_6N_2O_4$: C, 57.40; H, 2.63; N, 12.17. Found: C, 57.67; H, 2.93; N, 12.40.

Step B 7.0 g of 5-nitro-2-(2-furyl)benzoxazole and 1.4 g of $PtO_2$ are mixed together in 200 ml of abs. ethanol and hydrogenated at 50 psi. The ethanol is removed under vacuum and the resulting oil is dissolved in 200 ml of $CHCl_3$. This solution is then added slowly to a rapidly stirred mixture of 3.45 g of thiophosgene, 3.0 g of calcium carbonate, 20 ml of water and 150 ml of $CHCl_3$ at 0° to 5°C. After the addition, the reaction is allowed to warm to room temperature and stir overnight. The $CHCl_3$ layer is evaporated under vacuum and the resulting material is recrystallized from petroleum ether to yield 3.1 g of product, mp 135°–137°.

Anal. Calc'd for $C_{12}H_6N_2O_2S$: C, 59.50; H, 2.50; N, 11.57. Found: C, 59.22; H, 2.78; N, 11.37.

EXAMPLE 2

Isothiocyanic acid, 2-(2-thienyl)-5-benzoxazole ester

Step A 15.4 g of 4-nitro-o-aminophenol and 11.2 g of thiophenecarboxaldehyde are dissolved in glacial acetic acid (450 ml) and heated to 85°. 44.4 g of lead tetraacetate is dissolved in 400 ml glacial acetic acid by warming and added to the above solution. Heating is continued for 0.5 hr and the solution is cooled to room temperature, diluted with an equal volume of water and the dark precipitate is collected and washed with additional water. The crude product is dissolved in $CH_2Cl_2$ (800 ml) and heated with 2.0 g of "Darco" G-60, followed by evaporation of the $CH_2Cl_2$. The resulting material is recrystallized from ethanol-chloroform (3:1) to yield 12.4 g of 5-nitro-2-(2-thienyl)benzoxazole, mp 186°–188°.

Step B 4.9 g of 5-nitro-2-(2-thienyl)benzoxazole and 1.0 g of 10% palladium on charcoal are suspended in 150 ml of absolute ethanol and reduced at 55 psi. The catalyst is filtered from the solution, the EtOH is removed under vacuum and the resulting oil is dissolved in 200 ml of $CHCl_3$. This solution is added slowly to a rapidly stirred mixture of 2.30 g of thiophosgene, 2.0 g of calcium carbonate, 20 ml of water and 150 ml of $CHCl_3$ at 0° to 5°C. After the addition, the reaction is allowed to warm to room temperature and stir overnight. The $CHCl_3$ layer is evaporated under vacuum and the resulting material is recrystallized from pentane to yield 2.5 g of light brown powder, mp 155°–158°.

Anal. Calc'd for $C_{12}H_6N_2OS_2$: C, 55.80; H, 2.34; N, 10.85. Found: C, 56.07; H, 2.39; N, 10.78.

EXAMPLE 3

Isothiocyanic acid, 2-(5-methyl-2-thienyl)-5-benzoxazolyl ester

Step A 6.16 g of 4-nitro-2-aminophenol and 5.04 g of 5-methyl-2-thiophenecarboxaldehyde are dissolved in 300 ml of glacial acetic acid and the mixture is heated to 75°C. 17.8 g of lead tetraacetate is then added in small portions to the hot solution. After the addition is complete the solution is heated for an additional hour.

The solution is diluted with an equal volume of water and the precipitated product collected and washed with additional water. The crude material is dissolved in 400 ml of methylene chloride and dried and heated with approximately 2.0 g of "Darco G-60." The charcoal is filtered off and the filtrate is evaporated to approximately one-third its original volume and cooled. The precipitated product is collected and washed with a small amount of cold $CHCl_3$ and dried to yield 5-nitro-2-(5-methyl-2-thienyl)-benzoxazole 4.3 g, mp 163°–165°.

Anal. Calc'd for $C_{12}H_8N_2SO_3$: C, 55.38; H, 3.10; N, 10.76. Found: C, 55.56; H, 3.38; N, 10.64.

Step B 2.80 g of the above benzoxazole is suspended in 150 ml of ethanol and 0.56 g of 10% Pd/C is added. The mixture is hydrogenated at 60 psi. The catalyst is filtered off and the ethanol is evaporated under vacuum at 35°, yielding a light yellow crystalline solid which is immediately dissolved in 150 ml of $CHCl_3$ and added slowly to a mixture of 100 ml of CHCl₃, 1.3 g of SCCl₂, 1.1 g of CaCO₃ and 25 ml of water. After the addition is complete the reaction is allowed to stir overnight at room temperature.

The CHCl₃ layer is separated and evaporated to dryness to furnish 2.5 g of light brown solid which is recrystallized from petroleum ether to yield 2.1 g, mp 157°–160°.

Anal. Calc'd for $C_{13}H_8N_2SO_2$: C, 57.34; H, 2.97; N, 10.27. Found: C, 57.25; H, 3.25; N, 10.39.

EXAMPLE 4

Isothiocyanic acid, 2-(2-thienyl)-6-benzoxazolyl ester

A. 5-Nitro-2-(2-thienylideneamino)phenol 7.70 g of 5-nitro-o-aminophenol (0.05 mole) is mixed with 2-thiophenecarboxaldehyde (excess) and heated to 195°C for a period of 10 min. The dark red solution is then diluted with 25 ml of methanol and the precipitated product collected. Crystallization from ethanol yields 7.6 g of pure Schiff Base, mp 140°–142°(60%).

Anal. Calc'd for $C_{11}H_8N_2O_3S$: C, 53.23; H, 3.25; N, 11.29; S, 12.92. Found: C, 53.10; H, 3.55; N, 11.53; S, 13.13.

B. 6-Nitro-2-(2-thienyl)benzoxazole 6.50 g of the above Schiff Base (0.026 mole) is dissolved in 100 ml of acetonitrile by refluxing on the steam bath. To this refluxing solution 11.6 g of lead tetraacetate (0.026 mole) is added and the mixture heated for approximately 1 min. The inorganic material is removed by filtration and the acetonitrile solution cooled in an ice bath yielding 4.2 g of product (66%), mp 200°–209°. This material is crystallized from acetonitrile to yield 3.2 g of 6-nitro-2-(2-thienyl)benzoxazole, mp 208°–210°(50%).

Anal. Calc'd for $C_{11}H_6N_2O_3S$: C, 53.66; H, 2.46; N, 11.38. Found: C, 53.90; H, 2.76; N, 11.66.

C. Isothiocyanic acid, 2-(2-thienyl)-6-benzoxazolyl ester 3.1 g of 6-nitro-(2-thienyl)benzoxazole (0.013 mole) and 0.7 g of 10% Pd/C are suspended in 100 ml of abs. ethanol. The mixture is hydrogenated at an initial pressure of 60 psi over a period of 3 hr. The catalyst is removed and the ethanol evaporated under vacuum yielding the crude amine.

The above amine is dissolved in 75 ml of chloroform and added to the following mixture at 5°C: chloroform, 100 ml; water, 25 ml; thiophosgene, 1.5g (0.013 mole); calcium carbonate, 1.3 g (0.013 mole). After the addition is completed the reaction is allowed to stir overnight at room temperature. The chloroform layer is separated, dried over anhyd. MgSO₄, and evaporated yielding a light brown solid. This material is crystallized from petroleum ether yielding 0.51 g of product, mp 118°–120° (17%).

Anal. Calc'd for $C_{12}H_6N_2OS_2$: C, 55.80; H, 2.34; N, 10.85. Found: C, 55.60; H, 2.64; N, 10.85.

EXAMPLE 5

Isothiocyanic acid, 2-[5-(acetoxymethyl)-2-furyl]-benzoxazol-5-yl ester

A. 2-[5-(Acetoxymethyl)-2-furyl]-5-nitrobenzoxazole 6.28 g of 5-[[(2-hydroxy-5-nitrophenyl)imino]methyl]-furfuryl alcohol, acetate ester (0.02 mole) is dissolved in 250 ml of acetonitrile by warming on a steam bath. To this solution 8.88 g of lead tetraacetate (0.02 mole) is added and the solution then heated for one minute. The precipitated inorganic material is removed by filtration and the solution then cooled in an ice-bath yielding 3.8 g of dark solid. This material is dissolved in chloroform and heated with Darco. The Darco is removed and the chloroform evaporated under vacuum yielding 1.6 g of light brown powder, mp 184°–190° (27%).

B. Isothiocyanic acid, 2-[5-(acetoxymethyl)-2-furyl]-benzoxazol-5-yl ester 1.50 g of 2-[5-(acetoxymethyl)-2-furyl]-5-nitrobenzoxazole (0.005 mole) and 0.3 g of platinum oxide are suspended together in 100 ml of abs. ethanol and the mixture hydrogenated at an initial pressure of 55 psi. The catalyst is removed and the EtOH evaporated under vacuum yielding a dark brown oil which is dissolved in 60 ml of chloroform and added to the following rapidly stirred cold solution:

0.6 g of thiophosgene (0.005 mole), 0.5 g of calcium carbonate (0.005 mole), 150 ml of chloroform and 25 ml of water. The mixture is then allowed to warm to room temperature and stirred for 3 hr. The chloroform layer is separated and evaporated to dryness yielding a light brown solid. This material is crystallized from petroleum ether yielding 0.52 g of pale yellow solid, mp 120°–121° (33%).

Anal. Calc'd for $C_{15}H_{10}N_2O_4S$: C, 57.32; H, 3.20; N, 8.91. Found: C, 57.33; H, 3.24; N, 8.72.

EXAMPLE 6:

Isothiocyanic acid, 2-(5-methyl-2-furyl)-5-benzoxazolyl ester

A. 5-Nitro-2-(5-methyl-2-furyl)-benzoxazole 7.70 g (0.05 mole) of 4-nitro-2-aminophenol and 5.50 g (0.05 mole) of 5-methylfurfural are dissolved in 400 ml of 95% EtOH and refluxed overnight. The ethanol is removed and the resulting dark red oil is recrystallized from CH₃CN yielding golden plates of the Schiff Base, mp 190°–193°. This material is then dissolved in CH₃CN (200 ml) by heating and 22.2 g (0.05 mole) of lead tetraacetate added. Heating is continued for 5 min and then solution is diluted with an equal volume of water. The dark brown precipitate is collected, washed with water and recrystallized from CH₂Cl₂ and Darco G-60 yielding 6.1 g of product (50%), mp 182°–184°.

B. Isothiocyanic acid, 2-(5-methyl-2-furyl)-5-benzoxazolyl ester.

3.32 g (0.0013 mole) of 5-nitro-2-(5-methyl-2-furyl)-benzoxazole and 0.65 g of 10% Pd are suspended in 100 ml of abs. EtOH and hydrogenated at 65 psi over a period of 4 hr. The catalyst is removed and the EtOH evaporated under vacuum yielding a dark brown residue. The residue is dissolved in 150 ml of CHCl₃ and added dropwise to the following cold suspension: 1.5 g (0.013 mole) of thiophosgene, 1.3 g (0.013 mole) of calcium carbonate, 150 ml of CHCl₃ and 30 ml of water. After the addition is complete the mixture is warmed to room temperature and allowed to stir overnight. The CHCl₃ layer is then separated and evaporated to dryness yielding 1.4 g of a light brown solid (43%) mp 110°–121°. This material is then extracted with petroleum ether and the extracts then evaporated yielding a tan solid. This material is recrystallized from petroleum ether yielding 0.540 g of white powder, mp 130°–132°(16%).

EXAMPLE 7

Isothiocyanic acid, 2-(1-methyl-2-pyrrolyl)-5-benzoxazolyl ester

A. 2-(1-Methyl-2-pyrrolyl)-5-nitrobenzoxazole 4.62 g of 4-nitro-o-aminophenol (0.03 mole) and 3.27 g of N-methylpyrrole-2-carboxaldehyde (0.03 mole) are dissolved in 250 ml of 95% ethanol. The solution is allowed to stand at room temperature for 0.5 hr and the precipitated yellow crystals collected yielding 6.1 g of Schiff's base (83%), mp 164°–166°. 6.1 g of the above Schiff's base (0.025 mole) is dissolved in 250 ml of acetonitrile by warming on a steam bath. To this warm solution 12.5 g of lead tetraacetate (0.025 mole) is added and the solution heated for 1 min. The insoluble inorganic materials are removed by filtration and the solution cooled in an ice-bath yielding 3.4 g of yellow plates, mp 178°–183°. This material is crystallized from acetonitrile yielding 2.8 g of 2-(1-methyl-2-pyrrolyl)-5-nitrobenzoxazole (46%), mp 183°–185°.

Anal. Calc'd for $C_{12}H_7N_3O_3$: C, 59.26; H, 3.73; N, 17.20. Found: C, 59.16; H, 3.90; N, 17.39.

B. 5-Amino-2-(1-methyl-2-pyrrolyl)benzoxazole 1.5 g of 2-(1-methyl-2-pyrrolyl)-5-nitrobenzoxazole (0.006 mole) and 0.15 g of 10% Pd/C are suspended in 100 ml of 95% EtOH and hydrogenated at 50 psi over a period of 2.5 hr. The catalyst is removed and the EtOH evaporated under vacuum yielding a brown solid. Crystallization from methanol yields 1.15 g of tan crystals, mp 183°–185° (89%).

Anal. Calc'd for $C_{12}H_{11}N_3O$: C, 67.91; H, 5.20; N, 19.70. Found: C, 67.77; H, 5.22; N, 19.80.

C. Isothiocyanic acid, 2-(1-methyl-2-pyrrolyl)-5-benzoxazole ester 1.0 g of 5-amino-2-(1-methyl-2-pyrrolyl)benzoxazole (0.0047 mole) is dissolved in 50 ml of chloroform and slowly added to the following cold mixture: 0.54 g of thiophosgene (0.0047 mole), 0.47 g of calcium carbonate (0.0047 mole), 100 ml of chloroform and 25 ml of water. After the addition is complete the reaction is stirred at room temperature for 2 hr. The chloroform layer is separated, dried over anhyd. MgSO₄ and evaporated under vacuum yielding a light brown solid. This material is crystallized from petroleum ether yielding 0.650 g of tan crystals, mp 105°–106° (54%).

Anal. Calc'd for $C_{13}H_9N_3OS$: C, 61.16; H, 3.56; N, 16.46. Found: C, 61.02; H, 3.75; N, 16.19.

EXAMPLES 8 to 21

In a manner similar to the procedure described in Example 1, Step A, the o-aminophenol shown in Column A of Table I below is reacted with the aldehyde shown in Column B to form the nitro-benzoxazole shown in Column C.

In a manner similar to the procedure described in Example 1, Part B, the nitro-benzoxazole (Column C) is reduced to the corresponding amino-benzoxazole, which is converted to the isothiocyanobenzoxazole product shown in Column D.

TABLE I

| Example No. | Column A R² (position) | NO₂ (position) | Column B R¹ | Column C R² (position) | NO₂ (position) | R¹ | Column D R² (position) | SCN (position) | R¹ |
|---|---|---|---|---|---|---|---|---|---|
| 8. | Cl (5) | 4 | furyl-CH₃ | Cl (6) | 5 | furyl-CH₃ | Cl (6) | 5 | furyl-CH₃ |
| 9. | H | 4 | N-methylpyrrolyl | H | 5 | N-methylpyrrolyl | H | 5 | N-methylpyrrolyl |
| 10. | CH₃ (4) | 5 | C₂H₅ | CH₃ (5) | 6 | C₂H₅ | CH₃ (5) | 6 | C₂H₅ |
| 11. | CH₃O (4) | 5 | thiazolyl | CH₃O (5) | 6 | thiazolyl | CH₃O (5) | 6 | thiazolyl |

TABLE I-continued

| Example No. | Column A R² (position) | NO₂ (position) | R¹ | Column B R¹CHO | Column C R² (position) | NO₂ (position) | R¹ | Column D R² (position) | SCN (position) | R¹ |
|---|---|---|---|---|---|---|---|---|---|---|
| 12. | Cl (6) | 4 | cyclohexyl | | Cl (7) | 5 | cyclohexyl | Cl (7) | 5 | cyclohexyl |
| 13. | C₂H₅ (4) | 5 | thiazolyl | | C₂H₅ (5) | 6 | thiazolyl | C₂H₅ (5) | 6 | thiazolyl |
| 14. | F (5) | 4 | H | | F (6) | 5 | H | F (6) | 5 | H |
| 15. | C₅H₁₁ (6) | 4 | cyclopropyl | | C₅H₁₁ (7) | 5 | cyclopropyl | C₅H₁₁ (7) | 5 | cyclopropyl |
| 16. | C₄H₉ (4) | 6 | cyclohexenyl | | C₄H₉ (5) | 7 | cyclohexenyl | C₄H₉ (5) | 7 | cyclohexenyl |
| 17. | Br (5) | 4 | pyridyl | | Br (6) | 5 | pyridyl | Br (6) | 5 | pyridyl |
| 18. | C₃H₇O (6) | 5 | ethylpyridyl | | C₃H₇O (7) | 6 | ethylpyridyl | C₃H₇O (7) | 6 | ethylpyridyl |
| 19. | C₂H₅ (5) | 5 | oxazolyl | | C₂H₅ (5) | 6 | oxazolyl | C₂H₅ (5) | 6 | oxazolyl |
| 20. | H | 4 | pyrimidinyl | | H | 5 | pyrimidinyl | H | 5 | pyrimidinyl |
| 21. | C₃H₇ (4) | 5 | pyrazinyl | | C₃H₇ (5) | 6 | pyrazinyl | C₃H₇ (5) | 6 | pyrazinyl |

What is claimed is:
1. A compound of the structure

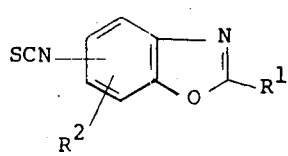

wherein R¹ is furyl, thienyl, or furyl or thienyl substituted with alkyl, halogen, acetoxyalkyl, or dialkylaminoalkyl, and R² is selected from the group consisting of hydrogen, alkyl, halogen, and alkoxy; wherein the terms alkyl and alkoxy refer to groups having up to 7 carbon atoms; and a physiologically acceptable acid-addition salt thereof.

2. A compound in accordance with claim 1 having the structure

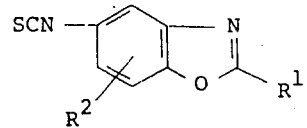

3. A compound in accordance with claim 1 having the structure

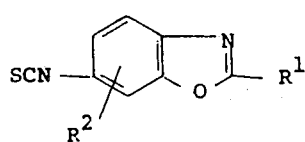

4. A compound in accordance with claim 1 having the structure

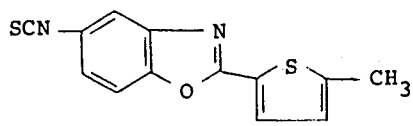

5. A compound in accordance with claim 1 having the structure

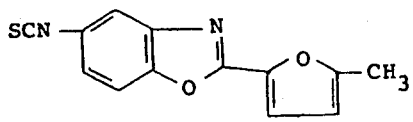

6. A compound in accordance with claim 1 having the structure

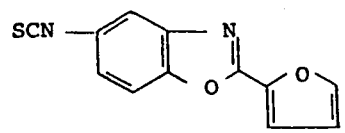

7. A compound in accordance with claim 1 having the structure

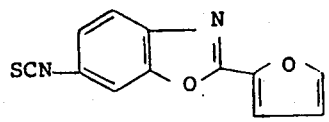

8. A compound in accordance with claim 1 having the structure

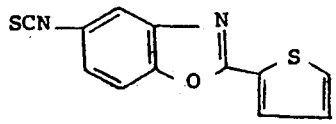

9. A compound in accordance with claim 1 having the structure

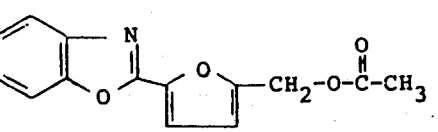

10. A compound in accordance with claim 1 having the structure

* * * * *